United States Patent [19]

Saaman et al.

[11] Patent Number: 5,750,138
[45] Date of Patent: May 12, 1998

[54] ADHESIVE PATCH FOR THE TRANSDERMAL ADMINISTRATION OF A MEDICATION

[75] Inventors: Ary Saaman; Patrick Poscio, both of Lausanne; Michael Graetzel, Saint-Sulpice, all of Switzerland

[73] Assignee: Westonbridge International Limited, Dublin, Ireland

[21] Appl. No.: 663,220

[22] PCT Filed: Dec. 13, 1994

[86] PCT No.: PCT/IB94/00416

§ 371 Date: Jul. 17, 1996

§ 102(e) Date: Jul. 17, 1996

[87] PCT Pub. No.: WO95/16439

PCT Pub. Date: Jun. 22, 1995

[30] Foreign Application Priority Data

Dec. 17, 1993 [CH] Switzerland .................. 3784/93

[51] Int. Cl.⁶ ............................................. A61F 13/02
[52] U.S. Cl. ............................................. 424/448; 424/449
[58] Field of Search .................................... 424/448, 449

[56] References Cited

U.S. PATENT DOCUMENTS

| 4,921,757 | 5/1990 | Wheatley et al. | 428/402.2 |
| 5,273,756 | 12/1993 | Fallon et al. | 424/448 |
| 5,284,660 | 2/1994 | Lee et al. | 424/449 |
| 5,362,308 | 11/1994 | Chien et al. | 604/20 |

FOREIGN PATENT DOCUMENTS

| 0 199 362 | 10/1986 | European Pat. Off. |
| 0 249 343 | 12/1987 | European Pat. Off. |
| 9204938 | 4/1992 | WIPO |
| 93 03692 | 3/1993 | WIPO |

*Primary Examiner*—D. Gabrielle Phelan
*Attorney, Agent, or Firm*—Young & Thompson

[57] ABSTRACT

An adhesive patch for delayed onset transdermal drug delivery, comprising a reservoir or matrix containing the drug. An impervious membrane is arranged on said reservoir or matrix and designed to become pervious after a given delay period by receiving an external stimulus that alters its physical/chemical structure.

5 Claims, No Drawings

ADHESIVE PATCH FOR THE TRANSDERMAL ADMINISTRATION OF A MEDICATION

FIELD OF THE INVENTION

This application is a 371 of PCT/IB94/00416, filed Dec. 13, 1994.

The present invention relates to an adhesive patch for the delayed transdermal administration of a medication, generally called a patch, which comprises in general a reservoir or a matrix containing said medication, as well as a removable protective strip, this protection being adapted to be removed just before placing the adhesive patch on the skin of the patient.

BACKGROUND OF THE INVENTION

Such a patch is well known and already used for the transdermal administration of different types of medications such as nitroglycerine, entofenamate, estradiol, scopolamine, dinitrate isorbide, clonidine, fentanyl, nicotine, etc., as described in the article by Richard W. Baker in "Controlled Released of Biologically Active Agents", J. Wiley & Sons, New York (1987), p. 239–45. There exist several types of such patches, also as disclosed in the above document, which also recites the advantages and drawbacks of this path of administration. In short, they can be divided into two large categories: (a) those which have a chamber serving as a reservoir for the medication, the latter being freed after removal of the protective strip before sticking the patch on the skin, either directly or through a microporous membrane, and (b) those which comprise a porous matrix, for example of silicone rubber or cellulosic ester, containing the medication which will diffuse into the skin from this support once the patch is in service position. Of course, other modifications of these patches are possible, for example by combining the two principal types above.

With most of the patches known at present, the administration of medication begins immediately after the protective band has been removed and the patch stuck to the skin, the speed of administration being of course a function particularly of the structure and of the nature of the porous membrane and/or of the support, as well as of the medication to be administered.

However, this peculiarity has been seen to be inconvenient when it is desired that this administration be delayed after emplacement of the patch. This is the case for example in the treatment of angina of the chest by means of nitroglycerine. Thus, an important element of this treatment is to be able to administer the nitroglycerine just before the client awakes, to prevent the effects of chest angina. It is therefore desirable in practice to have a patch whose effect is delayed for example 6 to 8 hours after its application.

The above object is at least partially achieved by transdermal administration systems disclosed in EP-A-0 199 362 and EP-A-0 249 343, which comprise means to delay said administration after emplacing the patch, in the form of an impermeable membrane device coacting with the reservoir or the matrix containing the medication to be administered, this device being so made that it becomes permeable in a delayed way by modification of its physico-chemical structure under the influence of an external stimulus.

However, the delay means such as are described in these two above documents have certain drawbacks, particularly for example the fact that the external stimulus is constituted by the body moisture, which is difficult to control, or else that the delaying effect is obtained by a phenomenon of diffusion through a membrane, which requires the use of relatively thick membranes for a delay of several hours.

SUMMARY OF THE INVENTION

Thus, the object of the present invention consists in providing an adhesive patch of the type recited, or patch, whose administration of the medication contained in this patch will be delayed in time, for example by several minutes or hours to several days, and which do not have the above drawbacks.

The adhesive patch for the transdermal administration of a medication, according to this invention and seeking to achieve the mentioned object, comprises a reservoir or a matrix containing said medication and an impervious membrane device coacting with said reservoir or matrix, this device being made such that it becomes permeable in a delayed manner by a modification of its physico-chemical structure under the influence of an external stimulus, is characterized by the fact that said membrane device comprises a membrane of the "off-on" type combined with a delay layer, said "off-on" membrane being a porous cellulose support on which is grafted a polymer sensitive to pH, and said delay layer consisting of a hydrolyzable ester in the form of a gel, and by the fact that it comprises a source of protons adapted to be placed in contact in service position with said delay layer, so as to serve as the external stimulus to trigger an autocatalytic process of hydrolysis of said ester.

On the other hand, according to a modification of the invention, a permeable membrane device can constitute a separate element, independent, which is adapted to be placed in contact with the reservoir or the matrix in service position, this reservoir or this matrix being adapted to be for example a patch of known type and available commercially.

DETAILED DESCRIPTION OF THE INVENTION

By way of example, there will be described hereinafter the principle usable to produce the present invention, more particularly to modify the permeability or the condition of aggregation of the membrane, as well as a practical use of the invention.

In the known case of a variation of pH, the principle consists in emitting protons to be able to destroy the membrane. This membrane must therefore be constituted of a structure sensitive to pH.

There could be used for the production of the membrane a polymer having contraction/expansion properties thanks to its ionizable functional groups. A polymer constituted for example of carboxylic groups has an extended structure at basic pH, because of its repulsion of the ionized groups. If pH is decreased, it contracts because the groups are protonated. The pores of the support, closed initially by the ionized polymer, become in that case accessible and the medication can be delivered. The membrane can also be constituted by a micellary/vesiculary layer. Upon changing the pH, the nature of the charge of the group of the tensioactive head is changed. This gives rise then to a modification of the electrostatic forces, and the vesicles are destroyed, rendering the membrane permeable. The tensioactive head groups used can be carboxylic, amine, pyridinium or sulfonic groups. Finally, the use of hydrogels containing ionizable groups is also possible. The presence of loaded monomers greatly increases the swelling power of these hydrogels. When the ionizable groups are in neutral form, the hydrogels cannot swell and are impermeable.

Upon changing the pH, the groups ionize and the hydrogels swell because of the repulsion forces. The membrane then becomes permeable to the medicating substance.

The kinetics of the autocatalytic reactions contemplated by the present invention lend themselves particularly well to the triggering of the opening of the membrane with delayed effect: after a period of induction, whose duration is adjustable by careful choice of the starting conditions, the speed of formation of the stimulus increases exponentially to reach its maximum after a predetermined time delay.

There is preferably used the combination of an "off-on" membrane whose permeability depends on the pH and on a delay layer in contact with the latter, for example in the form of a hydrogel, the opening of the membrane taking place under the influence of acidification of this delay layer by an autocatalytic process.

By way of example, the "off-on" membrane can be formed of a cellulose support on which is grafted an acrylic acid polymer; according to the value of the pH, the polymer changes structure and closes or not the pores of the support.

Thanks to the delay layer, it can be constituted by a hydrolyzable ester, preferably in the form of a gel, for example a polyacrylamide gel. The hydrolyzable ester could be a lactone of propionic acid or a gluconic acid. The delay action is thus obtained by hydrolysis of this ester, which tends to acidify in a controlled way the "off-on" membrane. This process is autocatalytic, because it produces itself the protons necessary for said hydrolysis. As to the initial source of protons necessary for triggering the process, it results from external stimuli, for example of the contact between the delay layer and the reservoir or the material containing the medication to be administered.

The present invention can be applied, for example, to a patch adapted to treat chest angina and containing therefore as active principle nitroglycerine, this base patch being adapted to be similar to those already commercialized. According to the invention, it will moreover be provided with an impermeable membrane, and for its use, the patch will be subjected to an external stimulus as described above, before or simultaneously with its emplacement on the skin of the patient, in its active service position. This stimulus will thus trigger a reaction which leads preferably in 6 to 8 hours to the destruction of the sensitive membrane, or to the opening of the pores of this latter, such that the medication contained in the patch will be liberated and transdermally administered to the patient. The duration of the delay effect which can be adjusted particularly by the number of layers, the thickness of these latter, or the porosity of the support, will thus permit the patient to apply the patch the evening before going to bed, such that its action can start just before waking up the next morning.

In practice, and by way of example, there has been made a delay device according to the invention, in a form separated in out-of-service position from the reservoir or from the matrix containing the medication to be administered transdermally, here nitroglycerine or trinitrin. One could if desired use as trinitrin matrix a patch available commercially, for example under the mark "DIAFUSOR"; such a transdermic device is constituted of an adhesive diffusion matrix (acrylic polymer, thickener, cross-linking agent) which contains the trinitrin in its mass and a flexible film support adapted for securing the adhesive (polyethylene-polyvinylidine coextruded thermoplastic material), the matrix being protected in out-of-use position for storage by a polyvinyl silicone film. This device is made to liberate transdermally an average dose of 5 mg, respectively of 10 mg, per 24 hours, and has an adhesive surface of 10 $cm^2$, respectively of 20 $cm^2$, the matrix containing 40 mg, respectively 80 mg of trinitrin.

The delay device according to the invention is constituted for example by a membrane of the "off-on" type formed by a cellulose support on which is grafted an acrylic polymer, whose structure is sensitive to pH, this membrane being disposed between a layer with retarding effect and an adhesive layer, these two layers being preferably in the form of gels and protected in out-of-service storage position each by a suitable protective film of known type.

The adhesive layer adapted to come into contact in service position with the skin of the patient, is formed for example of an aqueous acrylic emulsion, such as that known by the mark "GELVA" (Multipolymer Emulsion RA-3011) of the Monsanto company (USA).

As to the delay layer, it can be formed of polyacrylic gel containing in its mass a hydrolyzable ester, such as a lactone of gluconic acid.

Thus, in the case of use for the treatment of chest angina, the patient will use, before going to bed, a trinitrin patch, such as those now commercially available or another type, from which he will remove the protective film and which he will place on the delay layer of the device according to the invention also first stripped of its protective film; the assembly of the trinitrin patch and delay device will then be stuck to the skin of the patient after having removed the protection from the adhesive layer of the delay device.

The placing in contact of the matrix of the patch containing the trinitrin with the delay layer of the device according to the invention will then constitute the external stimulus necessary to trigger the process; thus, the matrix formed of a gel contains about 5% water, and will thus constitute a primary source of protons, the aqueous solution of trinitrin being in effect acid (about pH 4). These protons will trigger the hydrolysis reaction of the lactone present in the delay layer, this reaction being then autocatalytic. The delay layer will then acidify little by little, and after about 6 to 8 hours, will reach a pH below about 4.5, leading to the destruction of the structure of the acrylic polymer grafted on the "off-on" membrane and opening the pores of this latter, thereby giving passage to the trinitrin which will diffuse through the delay layer and reach after passage through the adhesive layer, the skin of the patient. Beginning at this time, the transdermal administration of the medication will take place normally, which is to say in the same manner as with a known patch. On the contrary, the beginning of this administration has been delayed voluntarily by 4 to 8 hours, preferably 6–8 hours, such that the effect of the trinitrin will begin before the patient wakes up.

Again by way of examples of practical applications, there can be cited the use of an adhesive patch according to the invention for the transdermal administration with delayed effect, for example by 4 to 6 or 8 hours, of a sleeping potion, which can be useful for persons who must avoid absorbing orally too strong a dose of sleeping potion or for those who have a certain tolerance for the sleeping potion whose effect is thus insufficient over time, or again of an anti-inflammatory agent, for example for the treatment of polyarthritis.

Of course, one skilled in the art will be able to do likewise in the production of the membrane, to choose the latter such that it does not interfere with the active principle to be administered or its support, and which has no toxic effects for the patient by contact with the skin or diffusion into the latter.

We claim:

1. Adhesive patch for the delayed transdermal administration of a medication comprising:

a reservoir or a matrix containing the medication; and a membrane device, the membrane device comprising:

a porous cellulose support upon which is grafted a polymer which is sensitive to pH; and a delay layer comprising a gelatinous hydrolyzable ester;

wherein the membrane device interacts with the reservoir or matrix such that the membrane device changes, after a delay period, from being impermeable to being permeable through modification of its physico-chemical structure, the delay period beginning when protons from the reservoir or matrix are brought into contact with the delay layer, the contact between the source of protons and the delay layer triggering an autocatalytic process of the hydrolysis of the ester.

2. Patch according to claim 1, wherein the hydrolyzable ester is a lactone of propionic or gluconic acid, and the gel is a polyacrylamide gel.

3. Patch according to claim 1, wherein the membrane device is adapted to be placed in contact with the reservoir or matrix and is initially separate from the reservoir or matrix, the membrane device having a first side adapted for said contact with the reservoir or matrix, and a second side having an adhesive layer adapted to contact skin of the recipient of the medication, the porous cellulose support being disposed between the delay layer and the adhesive layer.

4. Patch according to claim 3, wherein the delay layer is disposed on the first side of the membrane.

5. Delay device adapted to coact with an adhesive patch for delayed and controlled transdermal administration of a medication, the adhesive patch comprising a reservoir or a matrix containing the medication, wherein the delay device comprises:

a membrane, the membrane comprising a porous cellulose support onto which is grafted a polymer sensitive to pH; and a delay layer attached to the membrane, the delay layer comprising a hydrolyzable ester in the form of a gel;

wherein an autocatalytic process of hydrolysis of the ester begins when the delay layer is brought into contact with a source of protons, the process of hydrolysis converting the membrane over a period of time from being impermeable to being permeable, thereby allowing the delayed and controlled transdermal administration of the medication.

* * * * *